United States Patent [19]

Fites et al.

[11] Patent Number: 4,626,534
[45] Date of Patent: Dec. 2, 1986

[54] PHARMACEUTICAL FORMULATION

[75] Inventors: Alan L. Fites; Michael J. Pikal, both of Greenwood, Ind.

[73] Assignee: Eli Lilly and Company, Indianapolis, Ind.

[21] Appl. No.: 759,725

[22] Filed: Jul. 29, 1985

Related U.S. Application Data

[63] Continuation of Ser. No. 633,739, Jul. 23, 1984, abandoned.

[51] Int. Cl.$^4$ ............................................ A61K 31/545
[52] U.S. Cl. ..................................................... 514/203
[58] Field of Search ........................................ 514/203

[56] References Cited

U.S. PATENT DOCUMENTS 4,258,041 3/1981 O'Callaghan et al. ............... 514/203
4,329,453 5/1982 Brodie et al. ......................... 514/203
4,406,887 9/1983 Gordon et al. ....................... 514/203

FOREIGN PATENT DOCUMENTS 2126479 3/1984 United Kingdom ................ 514/203

Primary Examiner—Jerome D. Goldberg
Attorney, Agent, or Firm—William B. Scanlon

[57] ABSTRACT

Ceftazidime pentahydrate is formulated with a pharmaceutically acceptable base and amorphous lactose to provide stabilized pharmaceutically acceptable formulations.

6 Claims, No Drawings

PHARMACEUTICAL FORMULATION

This application is a continuation of application Ser. No. 633,739 filed July 23, 1984, now abandoned.

BACKGROUND OF THE INVENTION

This invention relates to pharmaceutical formulations. In particular, it relates to pharmaceutical formulations of the semi-synthetic cephalosporin antibiotic known as ceftazidime.

The antibiotic ceftazidime is described by O. Callahan, et al., in U.S. Pat. No. 4,258,041 and is chemically named (6R,7R)-7-[(Z)-2-(2-aminothiazol-4-yl)-2-(2-carboxyprop-2-oxyimino)acetamido]-3-(1-pyridiniummethyl)-3-cephem-4-carboxylate. Ceftazidime has been obtained as a crystalline pentahydrate, which is a useful form for pharmaceutical formulations of the antibiotic. Ceftazidime pentahydrate is described by Brodie, et al., in U.S. Pat. No. 4,329,453. It has been found that formulations of ceftazidime pentahydrate can degrade, particularly when stressed at higher than room temperatures, and that the degradation can lead to the development of high molecular weight polymer in the formulation. Degradation leading to polymers having a molecular weight of about 10,000 or greater have been observed to impart toxicity to the formulation. Further, such degradation diminishes the pharmaceutical elegance of the formulations and is to be avoided for that reason alone.

The formulations of ceftazidime pentahydrate provided by this invention suppress the formation of polymer having a molecular weight greater than about 10,000, even upon stress of the formulation, and, thus, provide a more pharmaceutically elegant product for administration.

SUMMARY OF THE INVENTION

Pharmaceutical formulations comprising ceftazidime pentahydrate in crystalline form, a pharmaceutically acceptable base, and amorphous lactose, are provided. The incorporation of amorphous lactose in formulations of ceftazidime pentahydrate suppresses the formation of polymeric substances, including polymers having a molecular weight of 10,000 or higher. The formulations provided herein are in solid form and are suitable for parenteral administration in antibiotic therapy upon dilution with a physiological diluent.

DETAILED DESCRIPTION OF THE INVENTION

During accelerated stability studies of the antibiotic ceftazidime pentahydrate it was found that degradation of the antibiotic occurred with formation of polymeric substances of unknown composition. Among the polymeric substances are those having a molecular weight of 10,000 or greater and materials containing such polymeric degradation products were found to exhibit toxicity in rabbits. Many preparations of ceftazidime pentahydrate maintained on long-term stability studies at ordinary conditions of temperature and humidity also exhibited degradation leading to polymer formation to a greater or lesser extent than occurred with the accelerated studies.

According to the present invention, the formulation of an amorphous lactose with crystalline ceftazidime pentahydrate suppresses and retards the degradation of the antibiotic and, in particular, degradation leading to polymeric substances having a molecular weight of 10,000 or greater. Thus, this invention provides a pharmaceutical formulation comprising ceftazidime pentahydrate, a pharmaceutically acceptable base, and amorphous lactose.

Lactose occurs in both an $\alpha$- and a $\beta$-form, either of which may be employed in the formulations of this invention, so long as the lactose is amorphous. The $\alpha$-lactose is commonly available and used in pharmaceutical formulations as the crystalline monohydrate. The crystalline monohydrate of $\alpha$-lactose is unsuitable as such in the formulations of this invention, however, it can be present in minor amounts in the amorphous form employed in the formulations of this invention. Preferably, the lactose, be it the $\beta$-form or the $\alpha$-form, is at least 90% in the amorphous form.

Since it appears that unbound water may be associated with the instability of ceftazidime, the amorphous lactose employed in the formulations desirably has a water content below about 3% to 5% by weight and preferably no more than about 1% and about 2% by weight. It appears that crystalline lactose monohydrate is ineffective in stabilizing ceftazidime since it has little tendency to absorb moisture as does the amorphous form.

The formulations of this invention comprise amorphous lactose in an amount corresponding to between about 10% and about 50% of the weight of ceftazidime pentahydrate employed in the formulation.

A pharmaceutically acceptable base is included in the formulation to provide sufficient base to form a water-soluble salt of ceftazidime. Suitable pharmaceutically acceptable bases include, for example, the alkali metal carbonates, such as sodium carbonate, potassium carbonate; the alkali metal bicarbonates, such as sodium bicarbonate and potassium bicarbonate; and other suitable bases, such as ammonium carbonate, and the like. The amount of base employed in the composition is an amount sufficient to form the salt form with the amount of ceftazidime present.

The ceftazidime formulations provided by this invention are prepared in a conventional manner. For example, the ceftazidime pentahydrate may be mixed in a blender with the base and the amorphous lactose and then the mix filled into vials. Alternatively, the ceftazidime pentahydrate may be filled into a suitable parenteral vial, followed by addition of the base and lactose without prior blending. It is preferable to intimately mix the ceftazidime pentahydrate with the pharmaceutically acceptable base, for example, sodium carbonate, and then to add the amorphous lactose to the blend. The lactose need not be thoroughly blended with the ceftazidime pentahydrate and base mix to effectively stabilize the formulation.

Amorphous lactose having a desired water content of less than 3% may be prepared in a number of ways, for example, by freeze drying an aqueous solution of lactose or by spray drying. Amorphous lactose obtained by freeze drying is preferred. Freeze-dried amorphous lactose is obtained, for example, by first preparing a solution of lactose in water having a concentration of between about 5 and about 15%. The solution is then frozen at a temperature of about $-40°$ C. and dried under a vacuum while the temperature of the frozen solution is maintained at a temperature between about $-30°$ and about $-38°$ C. When ice sublimation is completed, the amorphous lactose obtained is dried further at a higher temperature, for example, between about 40° and about 80° C. This process provides amorphous lactose having a water content of about 1% to about 2%. The bulk-powder density of the amorphous lactose prepared by freeze drying varies with the concentration of the aqueous lactose solution. The more concentrated lactose solutions provide amorphous lactose with higher bulk-powder density. Accordingly, a concentrated solution of lactose of about 15% by weight provides amorphous form of lactose with the highest bulk-powder density.

The pharmaceutical formulations of this invention preferably contain between about 10% and about 15% of dry powdered sodium carbonate and between about 10% and about 50% of amorphous lactose per weight of ceftazidime activity. One gram of ceftazidime activity corresponds to more than one gram of ceftazidime pentahydrate owing to the weight of water of hydration. This invention further provides antibiotic formulations of ceftazidime in dosage unit form. One such formulation comprises 1 g of ceftazidime activity, 116 mg of sodium carbonate, and 250 mg of amorphous lactose. Another dosage unit formulation comprises 1 g of ceftazidime activity in the form of ceftazidime pentahydrate, 116 mg of sodium carbonate, and 500 mg of amorphous lactose. A larger dosage unit formulation provided herein comprises 2 g of ceftazidime, 232 mg of sodium carbonate, and 500 mg of amorphous lactose.

The formulations of this invention are useful for administration by the parenteral route, for example, i.v. or i.m. For such administration they can be incorporated into rubber-stoppered glass vials or into plastic bags suitable for administration by the i.v. drip method. The formulations can be incorporated into glass vials and plastic bags by conventional filling procedures. Because of the ability of amorphous lactose to absorb moisture, the filling operation should be carried out in a dry atmosphere, for example, in an atmosphere having a relative humidity of about 20 to about 30% at room temperature.

The pharmaceutical formulations of this invention may be stored at room temperatures for extensive periods of time without the formation of degradation products, including polymeric substances having a molecular weight of 10,000 or greater. The amorphous lactose incorporated in the formulations of this invention suppresses the degradation of ceftazidime, including the development of the undesirable polymeric substances having a molecular weight of 10,000 or greater. For example, formulations of the invention comprising ceftazidime pentahydrate, dry powdered sodium carbonate, and 25% by weight of amorphous lactose or 50% by weight of amorphous lactose inhibited the development of the high molecular weight polymeric substances in accelerated stability studies carried out at 60° C. for three days. The control lot of ceftazidime plus sodium carbonate carried out in the same test showed the presence of 0.87% of polymeric substances having a molecular weight of 10,000 or greater. Both of the formulations of the invention comprising, respectively, 25% and 50% by weight of amorphous lactose per weight of ceftazidime activity assayed for only 0.12% polymeric substances having a molecular weight of 10,000 or greater.

The assay employed in determining the amount of high molecular weight polymer in the ceftazidime formulations employs gel chromatography (HPLC) using a gel having an exclusion limit of about 10,000. A suitable gel for use in the assay is Fractogel ® TSK HW-40 (Merck). The assay is carried out in a glass HPLC column measuring 50 cm in length by 0.9 cm i.d. packed with a gel in potassium phosphate solution. A 10 mg-sample of the ceftazidime formulation is dissolved in 5 ml of pH 7 phosphate buffer. The solution, 100 microliters, is injected and the column is run at a flow rate of 1 ml/min. The column is run at room temperatures, and a photometric detector suitable for use in HPLC applications is run at 0.1 AUFS at 210 nm.

The following examples further illustrate the present invention.

EXAMPLE 1

Preparation of Amorphous Lactose via Freeze Drying

A solution of lactose monohydrate in water having a concentration of between about 5% and about 15% w/w is poured into stainless steel pans prechilled to about −35° C. The freeze dryer shelf temperature is maintained at −40° C. until the solution is frozen. The drying chamber is evacuated and primary drying is conducted at a temperature below −31.5° C. (pan contents). The temperature of the pan contents (frozen solution) is maintained at a temperature of between about −33° C. and about −38° C. by control of the shelf temperature at between about −15° C. and about −18° C. and a chamber pressure of between about 60 microns and 70 microns. When ice sublimation is complete as indicated by the temperature readings of the pan contents, secondary drying is conducted at a shelf temperature of about 25° C. for 15 h and at about 40° C. for 3 h. The amorphous lactose obtained has a water content of between about 1% and about 2%.

The amorphous lactose is stored in water vapor tight containers or in a dry atmosphere to prevent absorption of moisture.

EXAMPLE 2

Crystalline ceftazidime pentahydrate is blended with 10% by weight of dry, powdered sodium carbonate and filled into glass vials to provide 1 gram of ceftazidime activity and 116 mg of sodium carbonate per vial. To each vial is then added 250 mg of amorphous lactose, and the vials are then closed with a butyl rubber stopper.

EXAMPLE 3

Ceftazidime pentahydrate is blended with 10% by weight of dry powered sodium carbonate and 50% by weight of amorphous lactose prepared by the freeze drying method described by Example 1. The blended mixture is then filled into vials each containing 1 g of ceftazidime activity, 116 mg of dry powdered sodium carbonate, and 500 mg of amorphous lactose.

We claim:

1. A pharmaceutical formulation comprising ceftazidime pentahydrate, between about 10% and about 15% by weight of ceftazidime activity of dry powdered sodium carbonate, and between about 10% and about 50% by weight of ceftazidime activity of amorphous lactose.

2. The formulation of claim 1 wherein amorphous lactose is present in an amount corresponding to about 25% by weight of ceftazidime activity.

3. The formulation of claim 1 wherein the amorphous lactose is present in an amount corresponding to about 50% by weight of ceftazidime activity.

4. The pharmaceutical formulation of claim 1 in unit dosage form comprising about 1 g of ceftazidime pentahydrate, 116 mg of dry powdered sodium carbonate, and about 250 mg of amorphous lactose.

5. The pharmaceutical formulation of claim 1 in unit dosage form comprising about 1 g of ceftazidime pentahydrate, 116 mg of dry powdered sodium carbonate, and about 500 mg of amorphous lactose.

6. The pharmaceutical formulation of claim 1 in unit dosage form comprising about 2 g of ceftazidime pentahydrate, about 232 mg of sodium carbonate, and about 500 mg of amorphous lactose.

* * * * *